United States Patent [19]

Homma

[11] 4,259,204

[45] Mar. 31, 1981

[54] SHAMPOO COMPOSITION

[75] Inventor: Itomi Homma, Funabashi, Japan

[73] Assignee: Kao Soap Co., Ltd., Tokyo, Japan

[21] Appl. No.: 154,685

[22] Filed: May 30, 1980

Related U.S. Application Data

[63] Continuation-in-part of Ser. No. 56,199, Jul. 10, 1979, abandoned.

[30] Foreign Application Priority Data

Jul. 13, 1978 [JP] Japan ................................. 53/85462

[51] Int. Cl.$^3$ .......................... C11D 1/38; C11D 3/26; C11D 7/32
[52] U.S. Cl. ...................... 252/174.16; 252/DIG. 13; 252/DIG. 14; 252/540; 252/549; 252/554; 252/559; 424/70

[58] Field of Search ................... 252/174.16, 540, 541, 252/549, 554, 559, DIG. 14, DIG. 13; 424/70

[56] References Cited

U.S. PATENT DOCUMENTS

| | | | |
|---|---|---|---|
| 4,132,679 | 1/1979 | Tsutsumi et al. | 252/174.16 |
| 4,139,485 | 2/1979 | Imukawa et al. | 252/174.16 |

*Primary Examiner*—Mayer Weinblatt
*Attorney, Agent, or Firm*—Blanchard, Flynn, Thiel, Boutell & Tanis

[57] ABSTRACT

A shampoo composition comprising an anionic phosphoric acid ester, ethylenediamine tetraacetic acid or alkali metal salt thereof and an anionic, nonionic or amphoteric surface active agent effective for shampooing hair.

7 Claims, No Drawings

SHAMPOO COMPOSITION

CROSS REFERENCE TO RELATED APPLICATION

This application is a continuation-in-part of Ser. No. 56,199, filed July 10, 1979, now abandoned.

The present invention relates to a shampoo composition. More particularly, the invention relates to a shampoo composition comprising a shampoo base, an anionic phosphoric acid ester surfactant and ethylenediamine tetraacetic acid or its alkali metal salt, which composition imparts to hair good adaptability to combing and brushing.

In conventional shampoo compositions, there have been used various shampoo bases. For example, there can be mentioned anionic surface active agents such as alkyl sulfate salts and polyoxyethylene alkyl sulfate salts, nonionic surface active agents such as polyoxyethylene alkyl ethers and fatty acid alkylol amides, amphoteric surface active agents such as alkyl betaines and alkylamine oxides, and mixtures thereof. Shampoo compositions comprising such shampoo bases, however, are still defective. First of all, in hair which has been treated with these shampoo compositions, water-washed and rinsed, there is left a so-called "stiff touch", and when the hair is half-dried with a towel or the like, it cannot be combed or brushed smoothly. Furthermore, even when the hair is completely dried, it is not well-arranged and a comb or brush does not run smoothly therethrough. Moreover, under a low humidity condition, static charges are readily generated by brushing, and hence, rising of hair, that is, hair fly, is caused and brushing becomes more troublesome. Such poor adaptability to combing or brushing at the time of hair washing or at the hair treatment after washing results in the occurrence of damage of hair, such as broken hair and split ends. Thus, a beautiful and wiry state is lost in the hair. Therefore, development of a shampoo composition free of these defects has been eagerly desired in the art.

I performed research with a view toward eliminating the foregoing defects involved in the conventional shampoo compositions, and to my great surprise, it was found that a shampoo composition comprising at least one known shampoo base selected from the group consisting of anionic surface active agents, nonionic surface active agents and amphoteric surface active agents, and containing incorporated therein, (a) 0.8 to 20% by weight, based on the shampoo composition, of at least one anionic phosphoric acid ester type surface active agent represented by the following general formula (1):

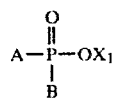

wherein A is

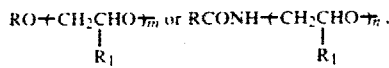

R is a linear or branched, saturated or unsaturated hydrocarbon group, preferably having an average carbon number of 10 to 18, $R_1$ is hydrogen or methyl, m is zero or a number of from 1 to 6, n is a number from 1 and 6 and the alkylene oxide units may be the same or different, B is $OX_2$ or A, and $X_1$ and $X_2$, which can be the same or different, are alkali metal, alkyl-substituted ammonium or hydroxyalkyl-substituted ammonium, and (b) 0.01 to 1.5% by weight of ethylenediamine tetraacetic acid (EDTA) or an alkali metal salt of ethylenediamine tetraacetic acid, has various excellent properties. More specifically, this shampoo composition is excellent in stability with the passing of time and in the foaming property, and hair washed with this shampoo composition has good adaptability to combing and brushing. Based on this finding, I have now completed the present invention.

As the anionic surface active agent, nonionic surface active agent or amphoteric surface active agent that is used as the shampoo base in the present invention, the following surface active agents can be mentioned.

(I) Anionic Surface Active Agents:

(a) Linear or branched alkylbenzene-sulfonate salts containing an alkyl group having an average carbon atom number of 10 to 16.

(b) Alkyl or alkenyl ethoxy-sulfate salts containing a linear or branched alkyl or alkenyl group having an average carbon atom number of 8 to 20 and also containing 0.5 to 8 moles on the average of ethylene oxide added, per molecule.

(c) Alkyl or alkenyl sulfate salts containing an alkyl or alkenyl group having an average carbon atom number of 10 to 20.

Olefin-sulfonate salts having 10 to 20 carbon atoms on the average, per molecule.

(e) Alkane-sulfonate salts having 10 to 20 carbon atoms on the average, per molecule.

(f) Saturated or unsaturated fatty acid salts having 10 to 20 carbon atoms on the average, per molecule.

(g) Alkyl or alkenyl ethoxy-carboxylic acid salts containing an alkyl or alkenyl group having an average carbon atom number of 10 to 20 and also containing 0.5 to 8 moles on the average of ethylene oxide added, per molecule.

(h) α-Sulfo-fatty acid salts or esters represented by the following formula:

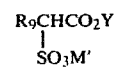

wherein Y stands for an alkyl group having 1 to 3 carbon atoms or a counter ion, M' stands for a counter ion, and $R_9$ stands for an alkyl or alkenyl group having 10 to 20 carbon atoms.

As the counter ions of the above-mentioned anionic surface active agents, there can be mentioned, for example, alkali metal ions such as sodium and potassium ions, alkaline earth metal ions such as calcium and magnesium ions, an ammonium ion and alkanol amines having 1 to 3 alkanol groups having 2 or 3 carbon atoms, such as monoethanolamine, diethanolamine, triethanolamine and triisopropanolamine.

(II) Nonionic Surface Active Agents:

(a) Polyoxyethylene alkyl or alkenyl ethers containing a primary or secondary alkyl or alkenyl group having an average carbon atom number of 8 to 20 and also containing 3 to 12 moles of ethylene oxide added.

(b) Polyoxyethylene alkylphenyl ethers containing an alkyl group having an average carbon atom number of 8 to 12 and also containing 3 to 12 moles of ethylene oxide added.

(c) Higher fatty acid alkanolamines or alkylene oxide adducts thereof represented by the following formula:

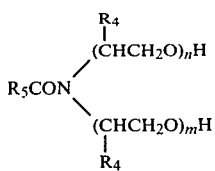

wherein $R_4$ stands for H or $CH_3$, $R_5$ stands for an alkyl or alkenyl group having 10 to 20 carbon atoms, n is an integer of from 1 to 3, and m is an integer of from 0 to 3.

(III) Amphoteric Surface Active Agents:

(a) Alkylamine oxides represented by the following formula:

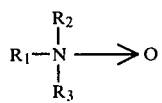

wherein $R_1$ stands for an alkyl or alkenyl group having 10 to 20 carbon atoms, and $R_2$ and $R_3$, which can be the same or different, stand for an alkyl group having 1 to 3 carbon atoms.

(b) Alkylbetaines or sulfobetaines represented by the following formula:

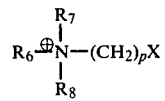

wherein $R_6$ stands for an alkyl or alkenyl group having 10 to 20 carbon atoms, $R_7$ and $R_8$ stand for an alkyl group having 1 to 4 carbon atoms, and X stands for the group $-COO^{\ominus}$ or $-SO_3^{\ominus}$.

(c) Imidazoline type amphoteric surface active agents represented by the following formula:

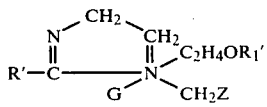

wherein R' stands for a fatty acid radical having an average carbon atom number of 10 to 20, $R'_1$ stands for H, Na or $CH_2COOMe$, Z stands for COOMe, $CH_2COOMe$ or

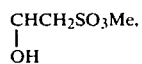

Me stands for Na, H or an organic base, and G stands for OH, an acidic salt of an anionic surface active sulfate or sulfoxide.

Among the foregoing shampoo bases, there are especially preferably employed such anionic surface active agents as linear alkyl sulfate salts having an average carbon atom number of 10 to 14 and polyoxyethylene alkyl sulfate salts containing an alkyl group having an average carbon atom number of 8 to 20 (the average mole number of added ethylene oxide being 0.5 to 8), higher fatty acid mono- or di-alkanolamides containing an alkyl group having an average carbon atom number of 10 to 14, alkylamine oxides containing an alkyl group having an average carbon atom number of 10 to 14, and amphoteric surface active agents of the alkylbetaine and imidazoline types.

In the present invention, an anionic phosphoric acid ester surface active agent represented by the above general formula (1) is incorporated into a shampoo base, such as mentioned above. In the general formula (1), as the alkali metal represented by $X_1$ and $X_2$, there can be mentioned lithium, potassium and sodium. In the process for the preparation of the anionic phosphoric acid ester salt represented by the general formula (1), an amine is used for neutralizing the corresponding phosphoric acid and after the neutralization step, this amine is quaternized and converted to a corresponding cation. This cation is an alkyl-substituted ammonium or hydroxyalkyl-substituted ammonium referred to in the general formula (1). Such amine includes primary, secondary and tertiary amines containing an alkyl or hydroxyalkyl group having 1 to 3 carbon atoms. As such amine, there can be mentioned, for example, dimethylmonoethanolamine, methyldiethanolamine, trimethylamine, triethylamine, dipropylamine, propyldimethylamine, monoethanolamine, diethanolamine, triethanolamine, isopropyldimethylamine and isopropylethanolamine. Among them, monoethanolamine, diethanolamine and triethanolamine are preferably employed, and triethanolamine is especially preferred.

As preferred examples of the anionic phosphoric ester type surfactant of the present invention, there can be mentioned sodium monoalkyl or monoalkenyl phosphates having 12 to 18 carbon atoms in the alkyl or alkenyl group, triethanolamine monoalkyl or monoalkenyl phosphates having 12 to 18 carbon atoms in the alkyl or alkenyl group, sodium and triethanolamine salts of polyoxyethylene ($\bar{p}=1.0-3.0$) monoalkyl or monoalkenyl phosphates having 12 to 18 carbon atoms in the alkyl or alkenyl group, sodium and triethanolamine salts of sesquialkyl or sesquialkenyl phosphates having 12 to 14 carbon atoms in the alkyl or alkenyl group, and sodium and triethanolamine salts of polyoxyethylene ($\bar{p}=1.0-3.0$) sesquialkyl or sesquialkenyl phosphates having 12 to 14 carbon atoms in the alkyl or alkenyl group.

Sodium ethylenediamine tetraacetate is preferably employed as the ethylenediamine tetraacetate in the present invention.

The main ingredient of the shampoo composition of the present invention, which is at least one member selected from anionic surface active agents, nonionic surface active agents and amphoteric surface active agents, should be incorporated in an amount of 1 to 30% by weight in the shampoo composition. The anionic phosphoric acid ester type surface active agent, which improves the adaptability of washed hair to combing and brushing, should be incorporated in an amount of 0.8 to 20% by weight, preferably 1 to 5% by weight, based on the shampoo composition, and ethylenediamine tetraacetate or its alkali metal salt should be incorporated in an amount of 0.01 to 1.5% by weight, preferably 0.05 to 0.5% by weight, based on the shampoo composition.

The composition of the present invention should be used in the form of a paste or liquid comprising water as a medium, and it is preferred that the pH of the paste or liquid be 4 to 8.

In addition to the above-mentioned indispensable ingredients, the shampoo composition of the present invention may comprise ingredients customarily used for conventional shampoo compositions, for example, dissolving agents such as propylene glycol, glycerin and urea, viscosity adjusting agents such as ethanol, inorganic salts, higher alcohols, hydroxyethyl cellulose and hydroxypropyl cellulose, perfumes, dyes, pigments, ultraviolet absorbers, antioxidants, dandruff removers, fungicides and antiseptics.

The present invention will now be described in detail by reference to the following Examples that by no means limit the scope of the invention.

In these Examples, % means percent by weight unless otherwise indicated.

EXAMPLE 1

Shampoo compositions comprising the ingredients shown in Table 1-1 were prepared, and the effects of the critical ingredients were examined. The results shown in Table 1-2 were obtained.

TABLE 1-1

| Ingredient | Composition (%) | | | |
|---|---|---|---|---|
| | Sample 1 | Sample 2 | Sample 3 | Sample 4 |
| triethanolamine lauryl sulfate | 20 | 20 | 20 | 20 |
| lauroyl diethanolamide | 3 | 3 | 3 | 3 |
| sodium polyoxyethylene-(3) lauryl phosphate* | 0 | 5 | 0 | 5 |
| disodium ethylenediamine tetraacetate | 0 | 0 | 0.25 | 0.25 |
| water | balance | balance | balance | balance |

Note
*monoester/diester = 74/26
The pH of each composition was adjusted to 7.2 by caustic soda or hydrochloric acid

TABLE 1-2

| Sample No. | Bubble Stability (1) | Comb through in dry state (2) | Hair Fly (3) |
|---|---|---|---|
| 4 (present invention) | 84 | 25 | ◎ |
| 1 (comparison) | 77 | (standard) | X |
| 2 (comparison) | 30 | 25 | Δ |
| 3 (comparison) | 79 | 2 | X |

Note
(1) Bubble Stability: A cylinder was charged with 100 ml of a 5% aqueous solution of the sample, and 0.5 g of refined hydrous lanolin was added as artificial soil to the solution. The solution was agitated at 1000 rpm for 5 minutes by using a horizontal propeller while the rotation direction was reversed at every 10 seconds. Just after stopping the rotation and also after 5 minutes' standing, the bubble volume was measured and the bubble stability index was calculated according to the following formula (the measurement was carried out at 40° C.):

$$\text{Bubble stability index} = \frac{\text{bubble volume after 5 minutes' standing}}{\text{bubble volume just after stopping of rotation}} \times 100$$

(2) Comb through: 30 g of human hair was wetted with water at 40° C., and was washed with 1 g of the sample and then rinsed twice. The hair was squeezed and set in a strain gauge. A comb was caused to run through the hair and the force imposed on the strain gauge was measured (in the wet state). The hair was dried by a drier, allowed to stand still overnight in a thermostat chamber maintained at a temperature of 25° C. and a relative humidity of 65% and then set in the strain gauge. The comb was caused to run through the hair and the force imposed on the strain gauge was measured (in the dry state). The comb running index was calculated according to the following formula:

$$\text{Comb running index} = \frac{(A - B)}{A} \times 100$$

wherein A stands for the force imposed on the strain gauge when the standard sample was tested and B stands for the force imposed on the strain gauge when the test sample was tested.

(3) Hair Fly: When the comb running in the dry state was examined in the above-mentioned manner, occurrence of hair fly by static charges generated was examined and the property was evaluated according to the following scale:
◎: hair fly was not caused at all
Δ: slight hair fly was observed
X: hair fly was observed The sample of the present invention was excellent in the bubble stability and the comb running, and occurrence of hair fly was completely prevented. Moreover, bubbles formed by the sample of the present invention were creamy and were excellent in the touch and feel.

EXAMPLE 2

A shampoo composition comprising the following ingredients was prepared, and the anionic phosphoric acid ester type surface active agent and sodium ethylenediamine tetraacetate were added in varying amounts to examine the changes of the effects caused by changes of the amounts of these ingredients.

| triethanolamine lauryl sulfate | 20% |
|---|---|
| lauroyl diethanolamide | 3% |
| Sodium polyoxyethylene(3) lauryl phosphate (monoester/diester = 74/26) | shown in Table 2 |
| disodium ethylenediamine tetraacetate | shown in Table 2 |
| water | balance |
| (pH was adjusted to 7.2) | |

TABLE 2

| Ingredient | Comparison | Amounts (%) Present Invention | | | | | Comparison | Present Invention |
|---|---|---|---|---|---|---|---|---|
| sodium polyoxyethylene-(3) lauryl phosphate | 0 | 5 | 5 | 5 | 5 | 5 | 5 | 0.5 | 1 |
| disodium ethylenediamine tetraacetate | 0 | 0.01 | 0.1 | 0.5 | 1.0 | 1.5 | 2.0 | 0.3 | 0.3 |
| comb running (in wet state) | standard | 20 | 25 | 27 | 24 | 18 | −6 | 3 | 15 |
| hair fly | X | ◎ | ◎ | ◎ | ◎ | ◎ | X | X | ◎ |

From the above results, it will readily be understood that when the amount of disodium ethylenediamine tetraacetate exceeds 1.5%, the comb running is drastically degraded and good results are not obtained.

EXAMPLE 3

Each of the various shampoo compositions of the present invention shown in Table 3 were excellent in the adaptability to combing and the hair fly-preventing effect.

TABLE 3

| Ingredient | Composition (%) Sample No. | | | | | |
|---|---|---|---|---|---|---|
| | 5 | 6 | 7 | 8 | 9 | 10 |
| sodium polyoxyethylene(3) lauryl ether sulfate | 8 | | | | | |
| coconut fatty acid diethanolamide | | 6 | 3 | 3 | 3 | 3 |
| triethanolamine lauryl sulfate | | | 20 | 20 | 20 | 20 |
| lauryl dimethylaminoacetyl betaine | 5 | | | | | |
| Miranol C2M* | | 7 | | | | |
| sodium lauryl phosphate (monoester/diester = 35/65) | 15 | | | | | |
| sodium polyoxyethylene(3) alkyl (average carbon number = 12.5) phosphate (monoester/diester = 75/25) | | | 3 | 4.5 | | |
| sodium polyoxyethylene(3) oleylcetyl phosphate | | | | | 3.0 | |
| lauroylamidoethyl polyoxyethylene(5) phosphate (monoester/diester = 60/40) | | | | | 3.0 | |
| polyoxypropylene(5) polyoxyethylene(1) cetyl ether phosphate | | | | | | 5.0 |
| disodium ethylenediamine tetraacetate | 0.5 | 0.25 | 0.25 | 0.3 | 0.3 | 0.3 |
| water | balance | balance | balance | balance | balance | balance |

(pH was adjusted to 7.2)

Note
*: imidazoline type amphoteric surface active agent manufactured and sold by Miranol Co., USA The embodiments of the invention in which an exclusive property or privilege is claimed are defined as follows:

1. A shampoo composition, consisting essentially of:
  A. from 0.8 to 20% by weight of at least one anionic phosphoric acid ester having the formula

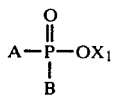

wherein A is

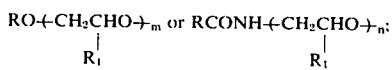

R is alkyl having an average carbon atom number of 10 to 18 alkenyl having an average carbon atom number of 10 to 18; $R_1$ is hydrogen or methyl; m is from 0 to 6; n is from 1 to 6; B is $-OX_2$ or $-A$; and $X_1$ and $X_2$, which can be the same or different, are hydrogen, alkali metal, alkyl ($C_1$-$C_3$)-substituted ammonium or hydroxyalkyl ($C_1$-$C_3$)-substituted ammonium;
  B. from 0.01 to 1.5% by weight of ethylenediamine tetraacetic acid or alkali metal salt thereof;
  C. from 1 to 30% by weight of at least one member selected from the group consisting of water-soluble anionic organic surfactant effective for washing hair and different from said anionic phosphoric acid ester, water-soluble nonionic organic surfactant effective for washing hair and water-soluble amphoteric organic surfactant effective for washing hair; and
  D. the balance is essentially water.

2. A shampoo composition as set forth in claim 1 wherein component C is at least one member selected from the group consisting of linear alkyl sulfates having an average carbon number of 10 to 14, alkylethoxy sulfates containing an alkyl group having an average carbon number of 8 to 20 and also containing 0.5 to 8 moles on the average of ethylene oxide units, fatty acid mono- and di-ethanolamides containing an alkyl group having an average carbon number of 10 to 14, alkylamine oxide amphoteric surface active agents, alkylbetaine amphoteric surface active agents and imidazoline amphoteric surface active agents.

3. A shampoo composition as set forth in claim 1 wherein component A is a monoalkyl anionic phosphoric acid ester.

4. A shampoo composition as set forth in claim 1 wherein component A is a monopolyoxyethylene-alkyl anionic phosphoric acid ester.

5. A shampoo composition as set forth in claim 1 wherein the amount of component A is 1 to 5% by weight and the amount of component B is 0.05 to 0.5% by weight.

6. A shampoo composition, consisting essentially of:
  A. from 0.8 to 20% by weight of at least one anionic phosphoric ester selected from the group consisting of sodium monoalkyl and monoalkenyl phosphates having 12 to 18 carbon atoms in the alkyl and alkenyl groups, triethanolamine monoalkyl and monoalkenyl phosphates having 12 to 18 carbon atoms in the alkyl and alkenyl groups, sodium and triethanolamine salts of polyoxyethylene ($\bar{p}$=1.0–3.0) monoalkyl and monoalkenyl phosphates having 12 to 18 carbon atoms in the alkyl and alkenyl groups, sodium and triethanolamine salts of sesquialkyl and sesquialkenyl phosphates having 12 to 14 carbon atoms in the alkyl and alkenyl groups, and sodium and triethanolamine salts of polyoxyethylene ($\bar{p}$=1.0–3.0) sesquialkyl and sesquialkenyl phosphates having 12 to 14 carbon atoms in the alkyl and alkenyl groups;
  B. from 0.01 to 1.5% by weight of ethylenediamine tetraacetic acid or alkali metal salt thereof;
  C. from 1 to 30% by weight of at least one member selected from the group consisting of water-soluble anionic organic surfactant effective for washing hair and different from said anionic phosphoric acid ester, water-soluble nonionic organic surfactant effective for washing hair and water-soluble amphoteric organic surfactant effective for washing hair; and
  D. the balance is essentially water.

7. A shampoo composition as set forth in claim 6 in which component B is disodium ethylenediamine tetraacetate.

* * * * *

UNITED STATES PATENT OFFICE
CERTIFICATE OF CORRECTION

Patent No. 4,259,204    Dated March 31, 1981

Inventor(s) Itomi Homma

It is certified that error appears in the above-identified patent and that said Letters Patent are hereby corrected as shown below:

Column 7, line 64;  after "18" insert ---or---.

Signed and Sealed this

Fourteenth Day of July 1981

[SEAL]

Attest:

Attesting Officer

GERALD J. MOSSINGHOFF

Commissioner of Patents and Trademarks